Figure 1:
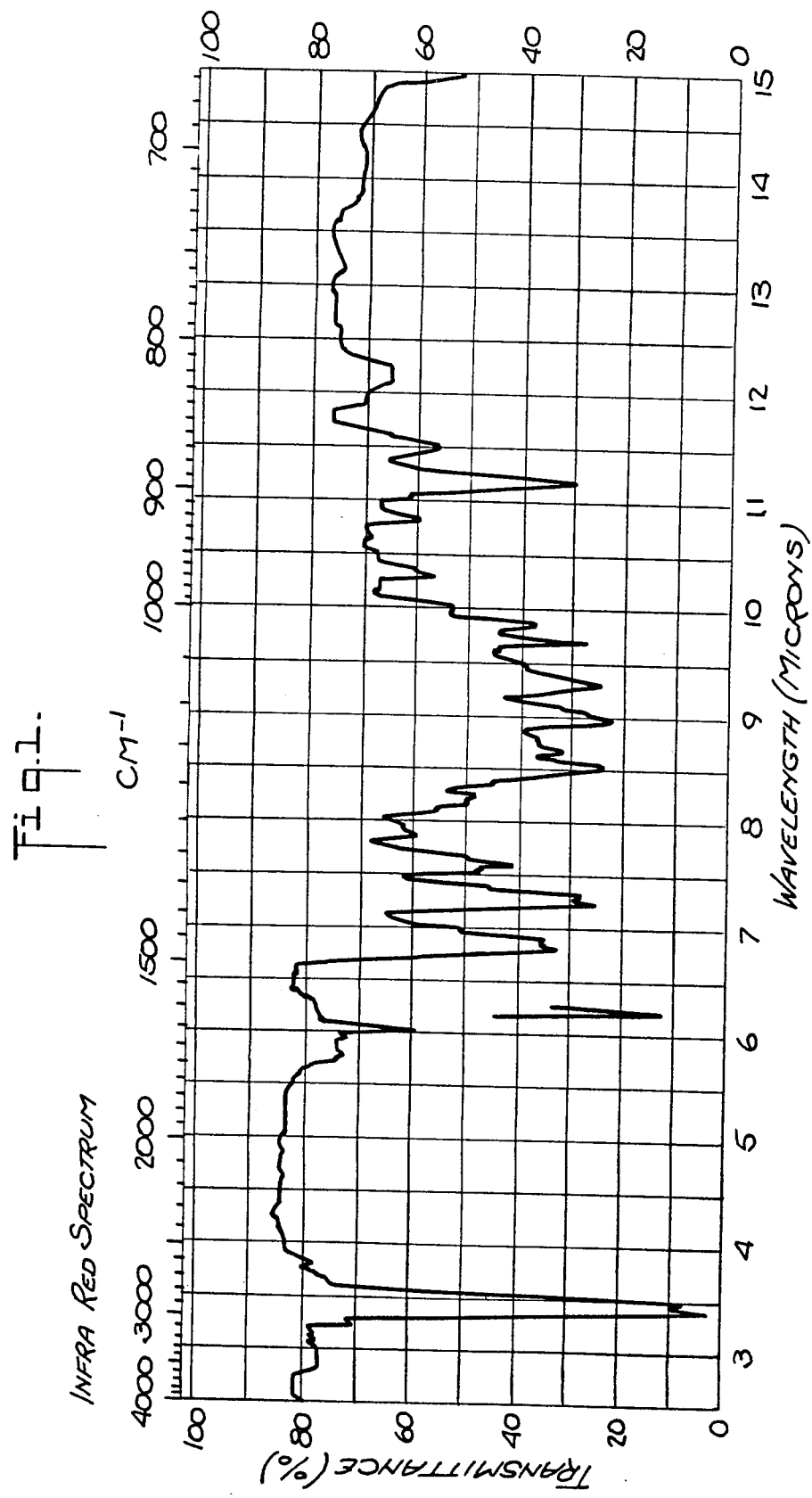

United States Patent [19]

Büchi et al.

[11] 4,271,048
[45] Jun. 2, 1981

[54] 9-HYDROXY-UNDECA-4,10-DIEN-1-AL

[75] Inventors: George H. Büchi; Hans Wüest, both of Cambridge, Mass.

[73] Assignee: Firmenich, S.A., Geneva, Switzerland

[21] Appl. No.: 176,790

[22] Filed: Aug. 11, 1980

[51] Int. Cl.³ ............................ A61K 7/46; C11B 9/00
[52] U.S. Cl. ................................. 252/522 R; 568/496
[58] Field of Search ...................... 252/522 R; 568/496

[56] References Cited

U.S. PATENT DOCUMENTS

| | | | |
|---|---|---|---|
| 3,382,276 | 5/1968 | Schenek et al. | 568/496 |
| 3,896,150 | 7/1975 | Hoffman | 252/522 R |
| 3,959,396 | 9/1976 | Ochsner et al. | 568/496 |
| 4,132,675 | 1/1979 | Naf | 252/522 R |

Primary Examiner—John F. Niebling
Attorney, Agent, or Firm—Pennie & Edmonds

[57] ABSTRACT

9-Hydroxy-undeca-4,10-dien-1-al, a novel unsaturated aliphatic hydroxy-aldehyde, has been found to possess useful odorous properties and consequently can be advantageously used as perfume ingredient.

3 Claims, No Drawings

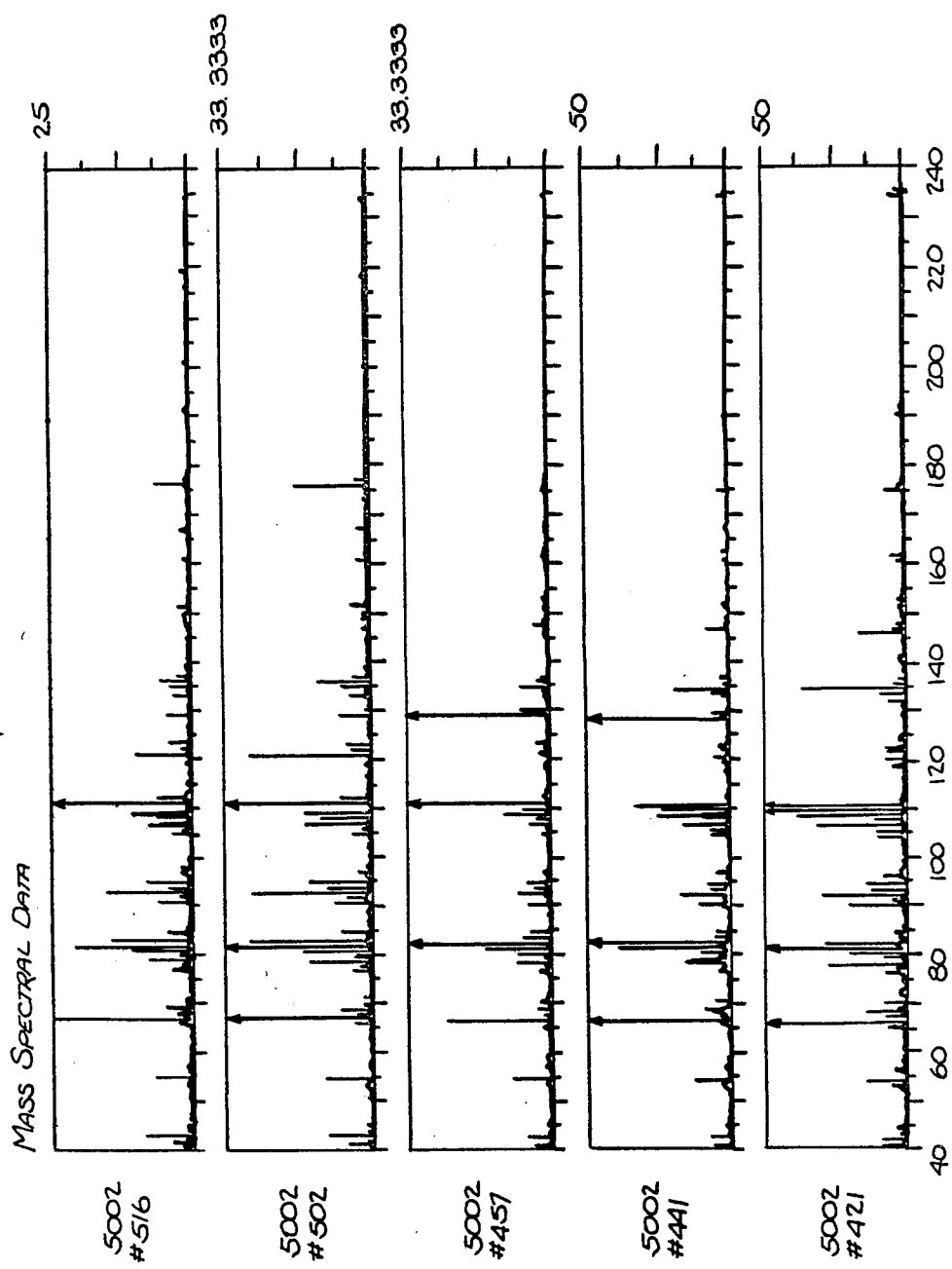

9-HYDROXY-UNDECA-4,10-DIEN-1-AL

THE INVENTION

An object of the present invention is to provide a novel composition of matter, namely an unsaturated aliphatic hydroxy-aldehyde of formula $$CH_2=CH-CH(OH)-(CH_2)_3-CH=CH-(CH_2)_2-CHO \quad (I)$$

or 9-hydroxy-undeca-4,10-dien-1-al.

A further object of this invention consists in a method for improving, enhancing or modifying the odorous properties of perfumes, perfume bases or perfumed products which method comprises the step of adding thereto a perfuming effective amount of 9-hydroxy-undeca-4,10-dien-1-al.

Finally the invention relates to a perfume or a perfume base containing a perfuming effective amount of the said hydroxy-aldehyde.

BACKGROUND OF THE INVENTION

9-Hydroxy-undeca-4,10-dien-1-al was first isolated as an unwanted by-product of an attempted double Claisen type reaction designed primarily to give the diene aldehyde of formula $$OHC-(CH_2)_2-CH=CH-(CH_2)_3-CH=CH-(CH_2)_2-CHO$$

a key intermediate for the synthesis of macrocyclic derivatives [see copending application Ser. No. 76,960].

We have surprisingly discovered that the isolated hydroxy-aldehyde possessed very interesting odorous properties and that consequently it could present a utility as perfume ingredient in general.

PREFERRED EMBODIMENTS OF THE INVENTION

Compound (I) presents in fact a fresh and clinging flowery scent reminiscent of the fragrance of petals. Its odour is both elegant and tenacious. Owing to its particular properties compound (I) finds a wide range of use, namely in compositions of floral-flowery type.

The proportions in which compound (I) of the invention can produce the desired perfuming effects can vary within wide limits. Typically, these proportions are of about 0.5 to 10, or even 20% or more by weight of the said compound based on the total amount of the perfume, perfume base or perfumed article into which it is incorporated. It has to be understood that the above proportions are not deemed to be interpreted restrictively and values lower or higher than the above given limits can be used whenever special effects are desired.

The preparation of compound (I) can be effected according to a method which consists in treating, with a vinyl-magnesium halide, glutaraldehyde to give 3,7-dihydroxy-nona-1,8-diene and converting this latter compound into the desired hydroxy-aldehyde by reacting it with ethylvinyl ether via a Claisen type rearrangement. This process is illustrated by the following reaction scheme 1:

Scheme 1

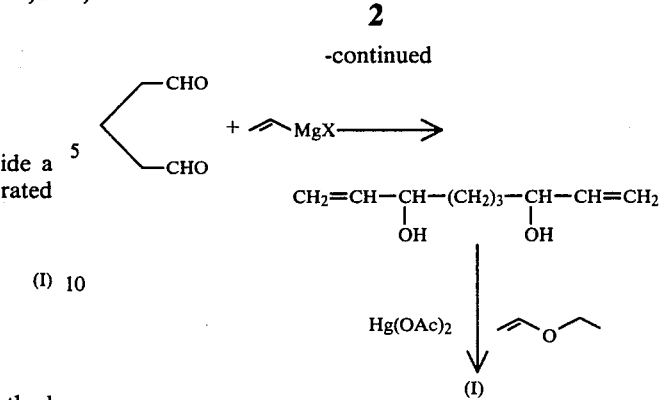

X = halogen
Ac = CH₃CO

Alternatively, compound (I) can be prepared via a Hoffmann type elimination of an amine quaternary salt according to the following reaction scheme:

Scheme 2

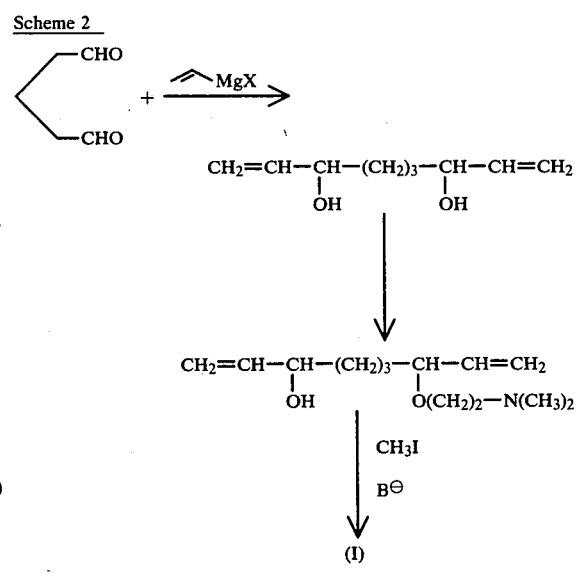

The examples which follow will indicate in a more detailed manner one of the methods used. Temperatures are indicated in degrees centigrade and the abbreviations have the meaning common in the art.

EXAMPLE 1

General

All solvents were dried and distilled before use. Each reaction was followed to completion by TLC and GC (where necessary) analysis. Work-up refers to (i) successive washing of the combined organic phase with H₂O, sat. aq. NaHCO₃ (omitted with acidic products) and sat. brine, (ii) drying of the organic phase with anhydrous Na₂SO₄ and (iii) removal of the solvent at reduced pressure (12 Torr unless stated otherwise). Melting points are uncorrected. TLC was performed using precoated silica plates (Merck: 60F-254), $R_F$ values being noted using an appropriate solvent, GC (using a Varian Aerograph 1700 or 2700) data records: nature of column, column temperature and retention time, ¹H-NMR, in CDCl₃ solution, (60 MHz spectrometer, Varian 60) data recorded in ascending ppm (δ) with tetramethylsilane (TMS) as the internal standard (=Oppm); chemical shifts, integration (nH) and multiplicity of each signal is given (s=singlet; d=doublet; t=triplet; q=quartet; m=multiplet; c=complex; b=broad signal); IR (as a thin film unless otherwise stated) (Perkin-Elmer A 21 spectrometer) data are given in descending cm$^{-1}$, the most important absorptions being chosen arbitrarily; mass spectral (m/e) (Atlas CH$_4$; electron energy: 70 eV) data are given in descending molecular weight; the abundance of each ion is noted as a percentage of the most abundant (=100%).

a. 3,7-Dihydroxy-nona-1,8-diene

A solution of glutaraldehyde[1] (83.6 g; 0.84 M) in THF (750 ml) was added dropwise, during 40 min., to a stirred solution of vinylmagnesium bromide [2 M; freshly prepared from Mg(48.6 g) and vinylbromide (239.4 g)] in THF (1.2 l) at 45° under N$_2$. After a further 20 min. the reaction mixture was poured, under N$_2$, onto a mixture of NH$_4$Cl (250 g) and ice-H$_2$O (1 l). Extraction (Et$_2$O), workup and fractional distillation in vacuo gave the title compound as a colourless oil (121 g) (93%), bp. 87°–89°/0.05 Torr, R$_F$=0.42 (EtOAc); GC (5% Carbowax ®) 240°/11 min., NMR (δ) 1.46 (c. 6H; aliphatic CH$_2$), 3.13* (bs, 2H; OH), 4.1 [c, 2H; CH(O)] and 4.9-6.2 (c, 6H, olefinic H) (*D$_2$O exchange removes this signal); IR (cm$^{-1}$) 3350 (b), 1645, 1430, 1080, 1000 and 925; m/e: 123 (9%), 110(12), 97(9), 81(22), 67(44), 57(83), and 54(100) [M+ (156) not observed].

(1) Commercial 50% aqueous glutaraldehyde was saturated with sodium chloride and extracted with CH$_2$Cl$_2$. The combined extracts were dried (Na$_2$SO$_4$), filtered and evaporated. Distillation gave glutaraldehyde, bp. 80°–82°/12 Torr.

b. 3-(2-Dimethylaminoethyl)-7-hydroxy-nona-1,8-diene

A stirred mixture of 3,7-dihydroxy-nona-1,8-diene (181.5 g; 1.16 M), 2-dimethylaminoethylchloride hydrochloride (201 g; 1.4 M), powdered NaOH (163 g; 4.07 M) and toluene (2.4 l) was refluxed during 4.5 h. The reaction mixture was cooled and washed successively with H$_2$O and sat. brine. Work-up and fractional distillation in vacuo (spinning band) gave the title compound as a colourless oil (142 g) (54%) bp. 85°–90°/0.05 Torr, GC (5% Carbowax ®) 240°/4.8 min., R$_F$ 0.38 [methanol/EtOAc (9:1]; NMR (δ) 1.5 (c, 6H; aliphatic CH$_2$), 2.21 [s, 6H; (CH$_3$)$_2$N], 2.49 (t, J 7 Hz, 2H; CH$_2$N), 3.16* (bs, 1H, OH), 3.15-4.2 [c, 4H, CH$_2$(O) and CH(O)] and 4.9-6.2 (c, 6H; olefinic H) (*D$_2$O exchange removes this signal); IR (cm$^{-1}$) 3400 (b), 3080, 1645, 1460, 995 and 920.

c. 9-Hydroxy-undeca-4,10-dien-1-al (I)

A solution of methyl iodide (140.7 g; 0.73 M) in acetone (150 ml) was added dropwise, during 30 min., to a solution of the product obtained sub letter b. above (152 g; 0.67 M) in acetone (700 ml) at 24°–27° (temperature maintained by external ice-bath). After 1 h the solvent was removed to give the crude methiodide salt of 3-(2-dimethylaminoethyl)-7-hydroxy-nona-1,8-diene (269 g). This was immediately taken up into CH$_3$OH (1 l) and passed through Amberlite ® IRA 400 (OH) (650 g) which was eluted with CH$_3$OH (6 l). Removal of solvent followed by heating the residue (3 l distillation flask) under 12 Torr until 120° resulted in decomposition (starting at 95°) and excessive foaming during 15 min. The residue was now transferred to a distillation flask (500 ml) and distilled (95°/0.1 Torr). The distillate (105 g) was taken up into xylene (500 ml) and refluxed during 30 min. under N$_2$. The reaction mixture was cooled, ether was added and the solution was washed successively with aq. 2 NH$_2$SO$_4$ (100 ml), sat. brine and sat. brine+aq. sat. NaHCO$_3$. Work-up, column chromatography [silica, cyclohexane/EtOAc (6:4)] and fractional distillation in vacuo gave I as a colourless oil (42 g) (34%), bp. 78°–80°/0.01 Torr; GC (5% Carbowax ®) 240°/5.9 min.; R$_F$ 0.30 [cyclohexane/EtOAc (6:4)]; NMR (δ) 1.2-2.6 (c, 10H; aliphatic and allylic CH$_2$), 4.1 [c, 1H; CH(O)], 4.9-6.2 (c, 5H; olefinic H) and 9.73 (c, 1H, CHO); IR (cm$^{-1}$) 3420 (b), 2730, 1722, 1643, 1430 and 995; m/e 151 (6%), 139(7), 120(8), 110(25), 82(39) and 71(100) [M+(182) not observed].

EXAMPLE 2

A base perfume composition of flowery type (lily-of-the-valley) was prepared by mixing together the following ingredients (parts by weight):

| | |
|---|---|
| α-Isomethyl-ionone | 500 |
| Phenyl-ethyl-alcohol | 40 |
| Hexylcinnamaldehyde | 30 |
| Citronellol | 30 |
| Geraniol | 30 |
| p-Methylphenylacetaldehyde 10%* | 30 |
| Linalol | 20 |
| Farnesol | 10 |
| α-Damascone 10%* | 10 |
| β-Damascone 10%* | 10 |
| Dodecanol 10%* | 10 |
| cis-Hexenyl acetate 10%* | 10 |
| Indol 10%* | 10 |
| Hedione ®[1] | 10 |
| Hex-3-cis-enol 5%* | 10 |
| cis-Methyl-jasmonate | 10 |
| Total | 770 |

*in diethyl phthalate
[1] origin : Firmenich SA, Geneva (Switzerland)

The addition to 77 parts of the above composition of 8 parts of 9-hydroxy-undeca-4,10-diene-1-al, resulted in a novel composition with possessed a richer and sweeter fragrance. Its character was moreover more natural and its top note was more elegant and clinging.

What we claim is:

1. 9-Hydroxy-undeca-4,10-dien-1-al.

2. Method for improving, enhancing or modifying the odorous properties of perfumes, perfume bases or perfumed products which comprises the step of adding thereto a perfuming effective amount of the compound of claim 1.

3. A perfume or a perfume base which contains a perfuming effective amount of the compound of claim 1.

* * * * *

UNITED STATES PATENT AND TRADEMARK OFFICE
CERTIFICATE OF CORRECTION

PATENT NO. : 4,271,048
DATED : June 2, 1981

INVENTOR(S) : George H. Buchi and Hans West

Figure 2:
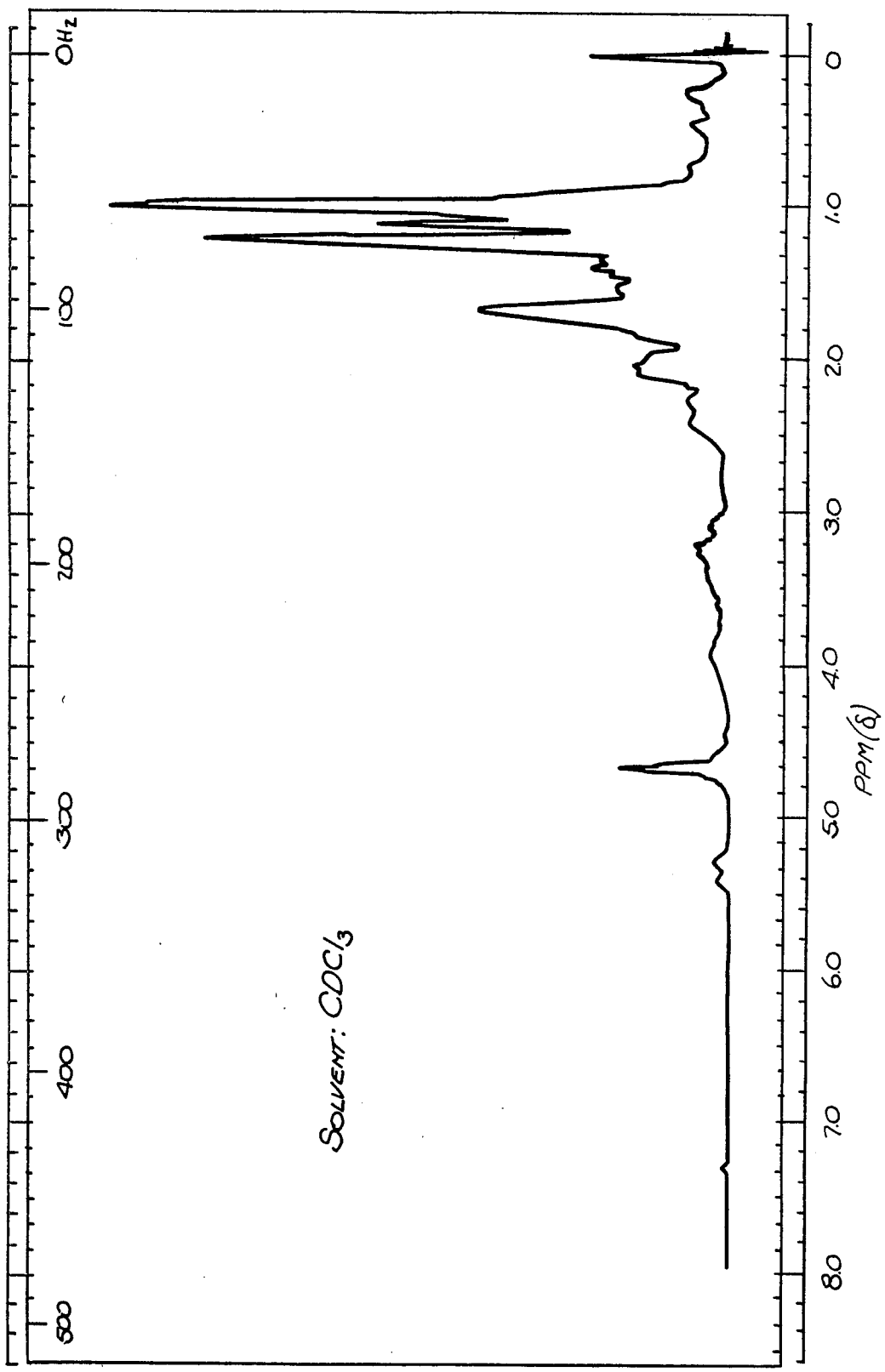
Figure 3:
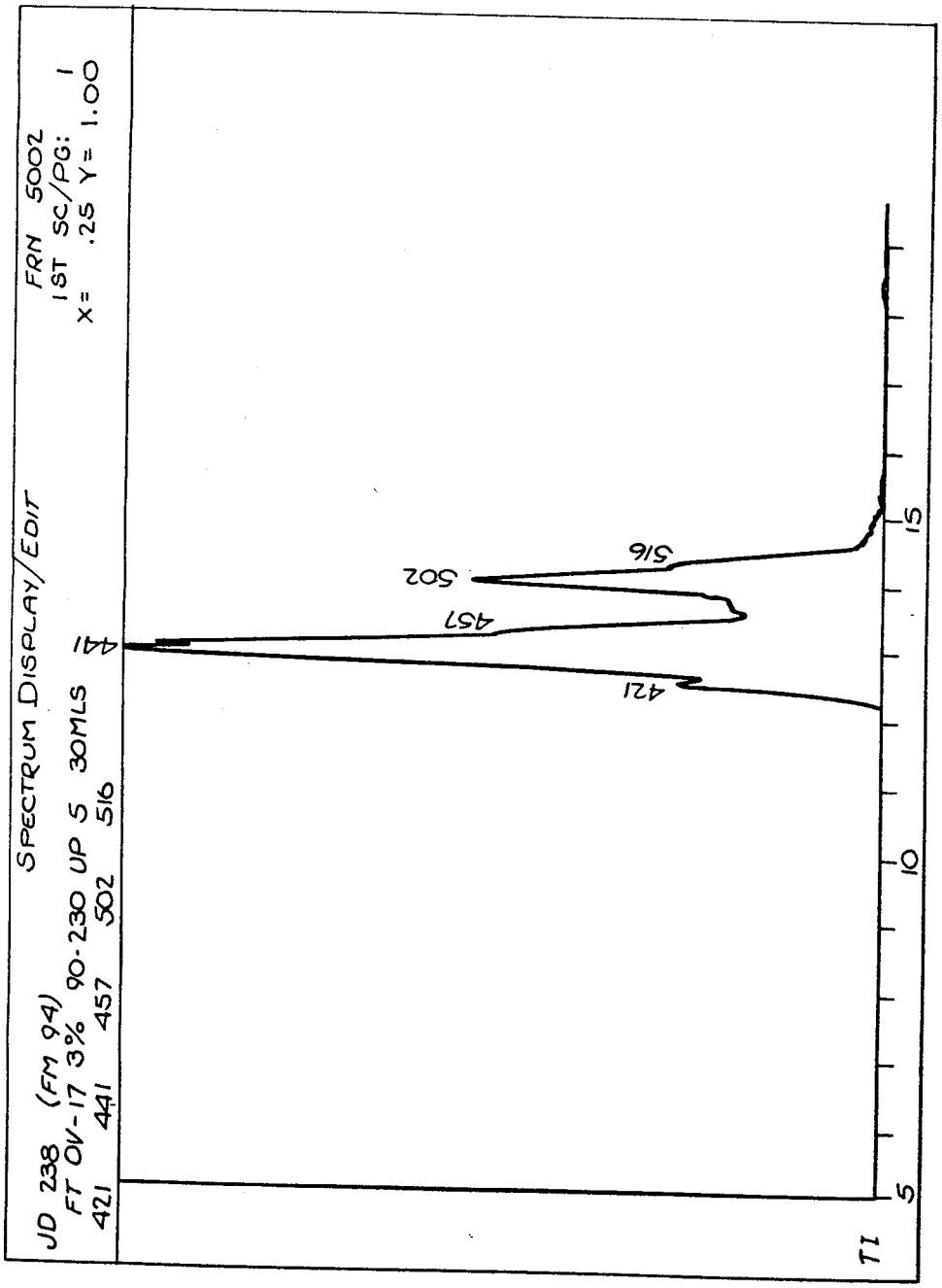

It is certified that error appears in the above-identified patent and that said Letters Patent are hereby corrected as shown below:

The sheets of drawings containing Figures 1 through 4 are to be cancelled.

Signed and Sealed this

Twenty-second Day of September 1981

[SEAL]

*Attest:*

GERALD J. MOSSINGHOFF

*Attesting Officer*     *Commissioner of Patents and Trademarks*